(12) United States Patent
Bayer et al.

(10) Patent No.: US 7,608,705 B2
(45) Date of Patent: Oct. 27, 2009

(54) OLIGONUCLEOTIDES, AGENTS CONTAINING THESE OLIGONUCLEOTIDES, AND THE USE THEREOF

(75) Inventors: Ernst Bayer, Tübingen (DE); Inge Bayer, legal representative, Tübingen (DE); Thomas Ketterer, Tübingen (DE); Holger Kalthoff, Hamburg (DE); Hendrik Ungefroren, Hamburg (DE); Michael Gerster, München (DE); Alexander Fiedler, Bonn (DE)

(73) Assignee: Universitatsklinikum Schleswig-Holstein, Kiel (DE)

( * ) Notice: Subject to any disclaimer, the term of this patent is extended or adjusted under 35 U.S.C. 154(b) by 159 days.

(21) Appl. No.: 10/381,869

(22) PCT Filed: Sep. 28, 2001

(86) PCT No.: PCT/EP01/11258

§ 371 (c)(1),
(2), (4) Date: Aug. 24, 2004

(87) PCT Pub. No.: WO02/26754

PCT Pub. Date: Apr. 4, 2002

(65) Prior Publication Data

US 2005/0019761 A1    Jan. 27, 2005

(30) Foreign Application Priority Data

Sep. 28, 2000   (DE) ................. 100 48 091

(51) Int. Cl.
    C07H 21/04    (2006.01)
(52) U.S. Cl. .............. 536/24.5; 536/24.31; 435/6; 435/325; 435/375; 514/44
(58) Field of Classification Search ............ None
    See application file for complete search history.

(56) References Cited

U.S. PATENT DOCUMENTS

| 5,245,022 | A * | 9/1993 | Weis et al. ............. 536/24.5 |
| 5,552,390 | A * | 9/1996 | Scholar et al. ............ 514/44 |
| 6,365,577 | B1 * | 4/2002 | Iversen .................. 514/44 |
| 6,395,492 | B1 * | 5/2002 | Manoharan et al. ........ 435/6 |
| 6,972,171 | B1 * | 12/2005 | Schlingensiepen et al. .... 435/6 |
| 2004/0241651 | A1 * | 12/2004 | Olek et al. ............. 435/6 |
| 2005/0019761 | A1 | 1/2005 | Bayer et al. |

FOREIGN PATENT DOCUMENTS

WO    WO-02/26754 A2    4/2002

OTHER PUBLICATIONS

Mier e tal. Preparation and Evaluation of Tumor-Targeting Peptide-Oligonucleotide Conjugates. Bioconjugate Chem 2000, Vo. 11:855-860.*

(Continued)

*Primary Examiner*—Kimberly Chong
(74) *Attorney, Agent, or Firm*—Lahive & Cockfield, LLP; Giulio A. DeConti, Jr., Esq.

(57) ABSTRACT

The invention relates to particular oligonucleotides, pharmaceutical agents that contain these oligonucleotides, and to the therapeutic use thereof. The oligonucleotides are, in particular, capable of inhibiting the proliferation of pancreatic tumors. These oligonucleotides thus have a therapeutic potential for the treatment of pancreatic tumors. This can involve, in the broadest sense, an antisense therapy.

2 Claims, 3 Drawing Sheets

CG = control group, TGI = treatment group I with ALZET®-pump,
TGII = treatment group II intraperitoneal injection

OTHER PUBLICATIONS

Neuzil et al. Induction of cancer cell apoptosis by alpha-tcopherl succinate: molecular pathways and structural requirements. FASEB 2001, vol. 15: 403-415.*

Mata et al. Evidence of Enhanced Iron excretion during systemic phosphorothiate oligodeoxynucleotide treatment. Journal of Toxicology 2000, vol. 38, No. 4.: 383-387.*

Sharp et al. Oligonucleotide enhanced cytotoxicity of Idarubicin for lymphoma cells. Leuk Lymphoma, 2001.*

Bayer, Ernst et al., "Synthesis of 3'-PEG-Modified Oligonucleotides on PS-PEG Tentacle Polymers," *Z. Naturforsch*, vol. 50b:671-676 (1995).

Fearon, Karen L. et al., "Investigation of the 'n-1' impurity in phosphorothioate oligodeoxynucleotides synthesized by the solid-phase β-cyanoethyl phosphoramidite method using stepwise sulfurization," *Nucleic Acids Research*, vol. 23(14):2754-2761 (1995).

Fiedler, Alexander et al., "Growth inhibition of pancreatic tumor cells by modified antisense oligodeoxynucleotides," *Langenbeck's Arch. Surg.*, vol. 383:269-275 (1998).

Hahn, Stephen A. et al., "Recent Discoveries in Cancer Genetics of Exocrine Pancreatic Neoplasia," *Digestion*, vol. 59:493-501 (1998).

Hirota, Yasuhide et al., "p53 Antisense Oligonucleotide Inhibits Growth of Human Colon Tumor and Normal Cell Lines," *Jpn. J. Cancer Res.*, vol. 87:735-742 (1996).

Lebedeva, Irina et al., "Cellular delivery of antisense oligonucleotides," *European Journal of Pharmaceutics and Biopharmaceutics*, vol. 50:101-119 (2000).

Maier, Martin et al., "Enzymatic Degradation of Various Antisense Oligonucleotides: Monitoring and Fragment Indentification by MECC adn ES-MS," *Biomedical Peptides, Proteins & Nucleic Acids*, vol. 1:235-242 (1995).

Manoharan, Muthiah et al., "Oligonucleotide Conjugates: Alteration of the PHarmacokinetic Properties of Antisense Agents," *Nucleosides & Nucleotides*, vol. 14(3-5):969-973 (1995).

* cited by examiner figure 1a: CG = control group, TGI = treatment group I with ALZET®-pump,
TGII = treatment group II intraperitoneal injection figure 1b: CG = control group, TGI = treatment group I with ALZET®-pump,
TGII = treatment group II intraperitoneal injection figure 2: CG = control group, TG = treatment group figure 3a: CG = control group, TGI = treatment group I 6mg/kg/d,
TGII = treatment group II 18mg/kg/d figure 3b: CG = Control group, TGI = treatment group I 6mg/kg/d,
BGII = treatment group II 18mg/kg/d

OLIGONUCLEOTIDES, AGENTS CONTAINING THESE OLIGONUCLEOTIDES, AND THE USE THEREOF

RELATED APPLICATION

The current application claims priority from the following International Patent Application filed pursuant to Patent Cooperation Treaty (PCT) on Sep. 28, 2001, designating the United States, which claims priority from German Patent Application S/N 100 48 091.8 DE filed on Sep. 28, 2000. The International Patent Application is assigned International Application Number, PCT/EP01/11258 and names all the same inventors as this applicatiom Ser. No. 10/381,869 entitled OLIGONUCLEOTIDES, AGENTS CONTAINING THESE OLIGONUCLEOTIDES, AND USE THEREOF. The International Patent Application was published in German on Apr. 4, 2002, and assigned International Publication Number: WO 02/026754.

BACKGROUND

The present invention relates to certain oligonucleotides, pharmaceutical agents containing these oligonucleotides, and the use thereof. The oligonucleotides are in particular able to inhibit the proliferation of pancreatic tumors. These oligonucleotides therefore have a therapeutic potential for the treatment of pancreatic tumors. This can involve, in the broadest sense, an antisense therapy.

Approximately 25,000 US citizens die from pancreatic cancer every year (A. Warshaw and C. Fernandez-del Castillo, New England J. Med. 326, 455 (1992)). Little is known about risk factors and the failure of radiation therapy and chemotherapy leads to a low 5-year survival rate after diagnosis.

Modified oligodeoxyribonucleotides (ODNs) have been found to be a group of very promising medicinal products in recent years and various mechanisms have been proposed for their mode of action. High expectations exist for the so-called antisense oligodeoxyribonucleotides (ASODNs) that suppress the expression of a specific protein, for example an oncogene.

Despite these high expectations and the in vitro demonstration that a specific gene is expressed to a lesser degree, only a single ASODN—Vitravene (ISIS, Carlsbad)—has been approved for use as a medicinal product.

On the other hand, oligodeoxyribonucleotides that do not have the sequence of an ASODN have been reported to have non-specific biological effects. The mechanism of action is not initially important for the development of a medicinal product, as long as the action can be clearly demonstrated in vivo and no side effects, or only justifiable ones, are seen.

Although a large number of modifications have been proposed and implemented in vitro for cell cultures (J. P. Shaw, K. Kent, J. Bird, J. Fischback, B. Froehler, Nucl. Acid Res. 19, 747 (1991), clinical studies and in vivo studies have been conducted almost exclusively with phosphorothioates in which an oxygen molecule has been replaced by a sulfur molecule in the phosphodiester linkages, on the assumption that such thioates will have a greater stability in the presence of nucleases, whilst being readily transported into cells. The half-life of normal phosphorodiester ODNs is on average 20-40 minutes, whereas the half-life of thioates is approximately 2-5 hours. This low increase in the stability of thioates may be the reason for the otherwise so promising model of antisense strategies in vivo not yet having led to a medicinal product. With a half-life of 2-5 hours, the bioavailability is too low and it remains to be seen what effects the shorter fragments, resultant upon degradation, will have.

It is known that ODNs with terminal modifications at the 3' and 5' position have a greater resistance to attack by exonucleases (M. Maier, K. Bleicher, H. Kalthoff, E. Bayer, Biomed. Peptd., Proteins & Nucl. Acids 1, 235 (1995)). Such modified ODNs have been used to date in cell cultures, but not in pre-clinical investigation models or clinical studies. In addition, most in vitro studies did not use phosphorothioates modified in the 3' and 5' positions, but instead the diester, so that endonucleases can still attack them. Lipophilic, cationic tensides, such as Lipofektin$^R$ are often added in vitro to improve uptake by cells. Such methods have not been adopted in vivo, or are markedly limited in scope, for various reasons, including the toxicity of such adjuvants.

It has now been found that the proliferation of human pancreatic tumors can be suppressed in vitro in cell cultures and in vivo in orthotopic xenotransplantation models using certain oligodeoxyribonucleotides, and in particular those oligonucleotides that have covalently-bound groups in the terminal 3' and/or 5' positions. In particular it was found that those sequences rich in C and G, or at least one CG motive, are especially effective in inhibiting the proliferation of pancreatic tumors in vivo.

SUMMARY OF THE INVENTION

The present invention therefore relates to the oligonucleotides described in the claims.

The term "oligonucleotide" refers to an oligomer of ribonucleic acid (RNA) or deoxyribonucleic acid (DNA) or mimetics thereof. These include oligonucleotides that comprise naturally-occurring nucleobases, sugars and covalent internucleoside linkages (backbone), as well as oligonucleotides with moieties that are not found in nature, but which have a similar function. Such modified oligonucleotides are preferred over native forms in accordance with the invention since they have desirable properties, for instance an elevated uptake by cells, a higher affinity for target nucleic acids and a greater stability in the presence of nucleases.

In particular, the nucleotides may have modifications or substitutions to the nucleobases (herein also referred to simply as "base"). The unmodified, or natural, nucleobases include the purine bases adenine (A) and guanine (G) and the pyrimidine bases thymine (T), cytosine (C) and uracil (U). The modified nucleobases (mimetics of natural nucleobases) include synthetic nucleobases such as 5-methylcytosine (5Me-C), 5-hydroxymethylcytosine, xanthine, hypoxanthine, 2-aminoadenine, 6-methyl derivatives and further alkyl derivatives of adenine and guanine, 2-thiouracil, 2-thiothymine and 2-thiocytosine, 5-halouracil and 5-halocytosine, 5-propinyluracil and 5-propinylcytosine, 6-azouracil, 6-azocytosine and 6-azothymine, 5-uracil (pseudouracil), 4-thiouracil, 8-halo-, 8-amino, 8-thiol-, 8-thioalkyl-, 8-hydroxyl- and further 8-substituted adenines and guanines, 5-halo-, in particular 5-bromo-, 5-trifluoromethyl- and further 5-substituted uracils and cytosine, 7-methylguanine and 7-methyladenine, 8-azaguanine and 8-azaadenine, 7-deazaguanine and 7-deazaadenine and 3-deazaguanine and 3-deazaadenine. Certain of these nucleobases are of particular use for increasing the binding affinity. These include 5-substituted pyrimidines, 6-azapyrimidines and N-2 substituted, N-6 substituted and O-6 substituted purines, for example 2-aminopropyladenine, 5-propinyluracil and 5-propinylcytosine. It was shown, for example, that 5-methylcytosine increases the stability of a nucleic acid duplex by 0.6-1.2° C.

C-rich oligonucleotides in which more than 40%, and preferably more than 50%, of the nucleobases are cytosine groups, or mimetics thereof, are suitable in accordance with the invention. Mimetics of cytosine groups in the above sense are modified nucleobases that have similar binding characteristics, i.e., above all the same specificity, but quite possibly a different affinity for complementary nucleobases. The same holds for mimetics of other nucleobases.

A suitable percentage of guanine, or mimetics thereof, is expedient in accordance with the invention. A ratio of C:G of 2:1 or above, and preferably of 3:1 or more, is an advantage.

In accordance with a special embodiment, oligonucleotides in accordance with this invention have at least one GC/CG motive, i.e., at least one cytosine group or a mimetic thereof is arranged in consecutive sequence to a guanine or a mimetic thereof.

Furthermore, a relatively low proportion, preferably below 15%, and in particular below 10%, of adenine or a mimetic thereof is expedient in accordance with this invention. In a special embodiment, oligonucleotides in accordance with this invention do not possess any adenine.

In general it is expedient if the oligonucleotides in accordance with this invention have 8 to 30, preferably 12 to 25 and in particular approximately 15 nucleobases.

The arrangement of nucleobases in oligonucleotides in accordance with this invention is generally guaranteed by the linkage of the nucleobases to one another in a suitable manner. In general this yields an oligomer with a consecutive sequence of nucleobases that are linked to one another through a backbone forming a main chain. Although linear oligomers are preferred, in certain cases branched, cyclic or even cross-linked structures are also suitable.

The oligonucleotides are generally nucleosides linked to one another, i.e., base-sugar combinations. The base component of the nucleotides is normally a heterocyclic base, in most cases a purine or pyrimidine. The nucleosides are generally linked to one another through a group covalently bound to the sugar portion of the nucleoside. In those nucleosides that have a pentofuranosyl sugar, this group may be bound to the 2', 3' or 5' hydroxyl group of the sugar. In general these groups covalently link neighboring nucleosides to one another to form a linear, oligomeric compound. The corresponding ends of this linear, oligomeric structure can in turn be linked together to form circular structures. Open, linear structures are preferred, however. The linking groups within the oligonucleotide structure are generally the internucleoside backbone of the oligonucleotide. The normal linkage or normal backbone of RNA and DNA are 3' to 5' phosphodiester linkages, i.e., the linking groups are phosphate groups.

Oligonucleotides that have a modified backbone or non-natural internucleoside linkages are preferred, though, in accordance with this invention.

Preferred, modified oligonucleotide backbones in particular include phosphorothioates, partially or completely sulfurated, for instance chiral phosphorothioates, phosphoromonothioates and phosphorodithioates. Further modified backbones are phosphorotriesters, aminoalkylphosphorotriesters, methylphosphonates and further alkylphosphonates, e.g., 3'-alkylenephosphonates and chiral phosphonates, phosphinates, phosphoramidates, e.g., 3-aminophosphoramidate and aminoalkylphosphoramidates, thionophosphoramidates, thionoalkylphosphonates, thionoalkylphosphotriesters and borophosphates with normal 3'-5' linkages, 2'-5' linked analogs thereof and those having an inverted polarity, in which neighboring pairs of nucleoside units are linked 3'-5' to 5'-3' or 2'-5' to 5'-2'. Various salts, mixed salts and the free acid forms are also included.

Special modified oligonucleotide backbones without a phosphorus atom are generally formed by short-chain alkyl or cycloalkyl internucleoside linkages that may also embrace heteroatoms or heterocycles. These include those having morpholino linkages (formed in part from the sugar portion of the nucleoside); siloxane backbones; sulfide, sulfoxide and sulfone backbones: formacetyl and thioformacetyl acetyl backbones; methylene formacetyl and thioformacetyl backbones; alkene-containing backbones; sulfamate backbones; methyleneimino and methylenehydrazino backbones; sulfonate and sulfonamide backbones; amide backbones; and others having mixed N, O, S and $CH_2$ component parts.

In further special oligonucleotides both the sugar and internucleoside linkage, i.e., the backbone, of natural nucleotide units, are modified. In antisense applications the bases are generally retained for hybridization with a suitable target nucleic acid. One such oligomeric compound, i.e., an oligonucleotide with exceptional hybridization properties, is referred to as a "Peptide Nucleic Acid" (PNA). In PNA compounds the sugar backbone of an oligonucleotide is replaced with an amide-like backbone, in particular an aminoethylglycine backbone. The nucleobases are retained and are bound directly or indirectly to the nitrogen atoms of the amide portion of the backbone.

Particularly-preferred embodiments of the invention are oligonucleotides with phosphorothioate backbones and, further, oligonucleosides with heteroatom backbones, in particular based on structural units such as —$CH_2$—NH—O—$CH_2$—, —$CH_2$N($CH_3$)—O—$CH_2$— [known as a methylene (methylimino) backbone or MMI backbone], —$CH_2$—O—N($CH_3$)—$CH_2$—, —$CH_2$—N($CH_3$)—N($CH_3$)—$CH_2$— or —O—N($CH_3$)—$CH_2$—$CH_2$—.

Modified oligonucleotides may also contain one or more substituted sugar moieties. For example, the 2' position may be substituted with OH, F, O-, S- or N-alkyl, O-, S- or N-alkenyl, O-, S- or N-alkinyl, or O-alkyl-O-alkyl, wherein the alkyl, alkanyl and alkinyl are preferably substituted or unsubstituted $C_1$-$C_{10}$-alkyl or $C_2$-$C_{10}$-alkenyl and alkinyl. Particularly preferred are substituents such as O[($CH_2$)$_n$O]$_m$$CH_3$, O($CH_2$)$_n$O$CH_2$, O($CH_2$)$_n$$NH_2$, O($CH_2$)$_n$$CH_3$, O($CH_2$)$_n$$NH_2$ and O($CH_2$)$_n$ON[($CH_2$)$_n$$CH_3$)]$_2$, where n and m are whole numbers from 1 to 10. Preferred modifications comprise an alkoxy-alkoxy group, for example 2'-methoxyethoxy (2'-O—$CH_2$$CH_2$O$CH_3$, also known as 2'-O-(2-methoxymethyl) or 2'-MOE). A further preferred modification includes 2'-dimethylaminooxyethoxy, i.e., a O($CH_2$)$_2$ON($CH_2$)$_2$ group, also known as 2'-DMAOE.

Further preferred modifications include 2'-methoxy (2'-O—$CH_3$), 2'-aminopropoxy (2'-O$CH_2$$CH_2$$CH_2$$NH_2$) and 2'-fluoro (2'-F). Similar modifications may also be made at other positions on the oligonucleotide, especially the 3' position of the sugar on the 3' terminal nucleotide, or in 2'-5' linked oligonucleotides, and the 5' position of the 5' terminal nucleotide. Oligonucleotides in accordance with this invention may also contain sugar mimetics such as cyclobutyl groups in place of the pentofuranosyl sugar.

Further modifications to oligonucleotides of the invention include the linkage of one or more groups or conjugates to the oligonucleotide to increase the activity, cellular distribution or cellular uptake of the oligonucleotides. Such groups include, above all, polyglycols, in particular polyalkyleneglycols, preferably polyethyleneglycols, peptides and, above all, lipophilic groups such as fatty acid groups with preferably 8 to 32 carbon atoms that may be saturated, monounsaturated or polyunsaturated, cholesterol, tocopherols, especially α-tocopherol and, above all, the naturally-occurring D-enantiomer thereof, or steroids, as well as derivatives thereof, in particular cholic acid, a thioether, e.g., hexyl-S-tritylthiol, a thiocholesterol, aliphatic chains, e.g., dodecandiol or undecyl groups, phospholipids, e.g., dihexyldecyl-rac-glycerol or tri-ethylammonium-1,2-die-O-hexadecyl-rac-glycero-3-H-phosphonate, polyamine chains, adamantane acetic add, palmityl groups or octadecylamine or hexylamino-carbonyl-oxicholesterol groups. The conjugates include for example, nanoparticles that may expediently have a positive charge. Diameters in the range 100 to 500 nm may be used. Polymers are used especially in this connection. Particles with a polystyrene or polyacrylate base are mentioned in particular.

Modification with lipophilic groups, above all in the 3' and 5' positions, increases bioavailability, because the half-life is extended by orders of magnitude against the attack of nucleases. Similar effects are achieved through the use of certain hydrophilic groups such as polyethyleneglycols, above all in the 3'-position. If the oligonucleotides in accordance with this invention are conjugated to nanoparticles that have a positive charge then the stability towards the attack of nucleases is also increased, both for unmodified phosphorothioate linkages and for oligonucleotides with terminal modifications and an excellent uptake in tumor cells observed.

Oligonucleotides in accordance with this invention that are particularly preferred are those with terminal modifications. Moreover, further modifications to the oligonucleotides of this invention may affect individual nucleosides, with a plurality of nucleosides modified differently or uniformly. Mixtures of oligonucleotides with different modifications are especially useful in terms of use in accordance with the invention.

The compounds in accordance with this invention can be made in a manner that is known. Known solid-phase synthesis systems may in particular be used. Suitable systems for synthesis are available commercially, for instance from Applied Biosystems (Foster City, Calif.) Accordingly, the compounds are synthesized in vitro.

Pharmaceutically acceptable salts, esters, a salts of such esters, or any other compounds which, upon administration in an animal, in particular humans, are capable of providing, directly or indirectly, the biologically active metabolites or a part thereof are also useful.

For instance, "Prodrugs" may be used. These are inactive forms of the active ingredient that are converted in vivo to an active form. Prodrug versions of oligonucleotides may be made available, for instance, as S-(acetyl-2-thioethyl)phosphate derivatives.

Pharmaceutically acceptable base addition salts include salts with metals or amines, such as alkali and alkaline earth metals or organic amines, especially cations such as sodium, potassium, ammonium, magnesium and calcium, or polyamines such as spermine and spermidine.

The pharmaceutically acceptable acid addition salts include salts with inorganic bases, e.g., hydrochloric acid, hydrobromic acid, sulfuric acid, phosphoric acid, nitric acid and the like, as well as with organic adds, e.g., acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalinesulfonic acid, methanesulfonic acid, p-toluenesulfonic acid, naphthalinedisulfonic acid, polygalacturonic acid, and the like.

Oligonucleotides with the sequences given below are examples that exhibit an excellent inhibition of the proliferation of human pancreas tumor cells:

```
5'-TGC TCC CCC CTG GCT-3'     (SEQ ID NO: 1)
5'-CCT CGC TTC GCC CGT-3'     (SEQ ID NO: 2)
```

Of particular advantage are the corresponding phosphorothioates. Modification at the 3' position with polyethyleneglycol (MW 1500) and at the 5' position with α-tocopherol brings additional advantages. SEQ ID NO: 1 is an example of an antisense oligonucleotide for the suppression of gene expression of the mutated p53 protein, whilst SEQ ID NO: 2 is an example of a sequence chosen from a randomized oligonucleotide library. Further sequences may be chosen from antisense sequences or randomized oligonucleotide libraries within the framework of the invention and modified if necessary, in particular through application of one or more of the following selection criteria:

Inhibition of the proliferation of growth of pancreas tumor cells through determination of 3H thymidine incorporation;

Stability of the construct against attack by endonucleases and/or exonucleases by measurement of the half-life of the oligonucleotides using capillary electrophoresis;

Determination of the uptake of the oligonucleotides in cells using confocal Laser Scanning microscopy;

Induction of apoptosis.

A further object of the present invention is the use of a compound in accordance of the invention to inhibit the proliferation of tumor cells.

This use also embraces a method for inhibiting the proliferation of tumor cells, in which at least one oligonucleotide in accordance with the invention is allowed to act on tumor cells. This method can be performed in principle in vitro, ex vivo or in vivo. Corresponding systems, e.g., in the form of cells or tissue, can be made available as a culture in vitro or ex vivo. Usage in vivo generally involves the administration of the oligonucleotide to the target individual.

Such tumor cell systems can be made available by an expert in the usual way. In particular, techniques are known to bring about corresponding degeneration of organisms and cells, for instance via recombinant techniques. Culture of organisms, cells or tissues in a suitable manner and assessment of proliferation in particular qualitatively, and if desired quantitatively, on the basis of suitable assays is also generally known to those skilled in the art. In particular it is a question of optimization of the method and the choice of suitable conditions under which the action of oligonucleotides in accordance with this invention bring about a modulation of proliferation.

The administration of oligonucleotides in accordance with this invention to an individual can be accomplished by those skilled in the art. As a rule, the individual is given a certain quantity of at least one of the oligonuclotides in accordance with this invention, generally formulated for corresponding pharmaceutical or veterinary use.

Consequently, the present invention also relates to agents, and in particular pharmaceutical agents, that comprise at least one oligonucleotide in accordance with this invention, as well as suitable auxiliary agents where desired, that in particular form a pharmaceutically acceptable formulation basis. The manufacture of such agents is known to someone skilled in the art.

The oligonucleotides in accordance with this invention can be used within the framework of these uses and processes, for instance for scientific purposes. Above all, the compounds in accordance with this invention can be used for therapeutic purposes.

Therapeutic uses of particular importance relate to the treatment of tumors. Treatment here means preventive/prophylactic avoidance or at least delay in terms of time, or alleviating or treating acute or chronic disease, i.e., in particular reducing, and optionally suppressing, the proliferation of the tumor and thus reducing the dissemination of the tumor and thus the risk of, or incidence of, metastases that derive from the primary tumor.

The subject of the present invention is therefore also the use of at least one compound in accordance with this invention for the treatment of tumors. This usage also embraces a method by which an effective quantity of at least one compound in accordance with this invention is administered to an individual to be treated, especially a human or an animal of commercial importance or a pet. Administration is generally once or several times a day, optionally at the same time as other active ingredients, or preparations containing active ingredients, or alternating with them. In this sense, the therapy may embrace the use of further treatment measures, for instance chemotherapy through the administration of cytostatic agents or radiotherapy.

Special advantages are seen in the treatment of pancreatic tumors, particularly in humans.

BRIEF DESCRIPTION OF THE DRAWINGS

An illustrative embodiment of the present invention will be described below relative to the following drawings.

DETAILED DESCRIPTION

Figure 1:
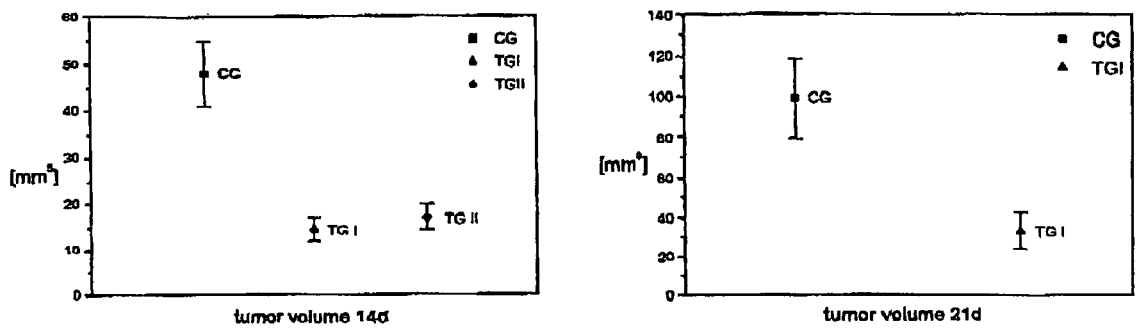
FIG. 1a is a graphical representation of changes in volume of selected groups of tumors treated with an exemplary oligonucleotide in accordance with an illustrative embodiment of the present invention.
FIG. 1b is a graphical representation of changes in weight of selected groups of tumors treated with an exemplary oligonucleotide in accordance with an illustrative embodiment of the present invention.
Figure 1:
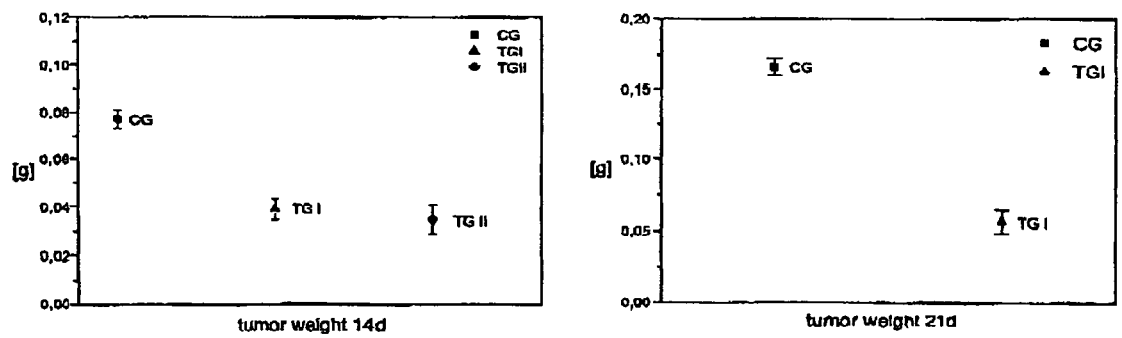

The present invention is now discussed in more detail by reference to the examples below.

EXAMPLE 1

Method Section

Syntheses

The modified ODNs were produced using an Applied Biosystem Model 394 DNA/RNA Synthesizer with TentaGel (Rapp Polymere Tübingen) as the carrier. Modified protocols for synthesis using Tentagel have been described in the literature (E. Bayer, M. Maier. K. Bleicher. H.-J Gaus, Z. Naturforsch. 50b, 671-676 (1995). PEG, fatty acid groups, cholesterol and tocopherol groups were introduced on the 5' terminal as phosphoramidates in $CH_2Cl_2$/acetonitrile (0.1 M). TETD (ABI, Welterstadt) was used primarily as the sulfurating agent. The DMT-protected ODNs were purified using HPLC: 15 min. linear gradient 20-80% acetonitrile in 0.1 M trimethylammoniumacetate, flow rate 1 ml/min, column Nucleosil 100 C18, 250×4 mm, a flow rate of 15 m/min, column GROM-SIL 100 ODS2 FE, 250×20 mm (Grom, Herrenberg).

Cell Cultures and Cell Uptake

The cell lines Panc-Tu-I, Panc-Tu-II, A818-4 and HPAF were used above all as human pancreatic tumor cells. The uptake of modified ODN by the cells was evaluated using confocal laser microscopy.

Measurement of Proliferation In Vitro

Cell suspensions ($7 \times 10^4$ cells $ml^{-1}$) were introduced into each well of a 96-well microtiter plate (Nunc, Wiesbaden). The medium was changed after 24 hours and the cell cultures (with corresponding ODN treatment and the controls without treatment) were labeled in 100 µl runs with 10 µl medium containing 7.4 kBq methyl-3H-thymidine (Amersham, Braunschweig) during the last 3 hours of the specified incubation times. The cells were then harvested and the radioactivity measured using a liquid scintillation counter.

The p53 protein was also determined in vitro using ELISA or Western Blot.

In Vitro Investigations in SCID Mice

Female SCID mice aged up to 8 weeks were used. A laparotomy was performed and $1 \times 10^6$ PancTu-I cells were injected into the pancreas under anesthesia. One group was given the ODN subcutaneously (using an implanted continuous ALZET® pump) and the other group was given ODN intraperitoneally once a day at a concentration of 6/18 mg/g body weight. The mice were then euthanized after 14 or 21 days. The pancreatic tumors were weighed, and measured to calculate the volume using the formula $\pi/6 \times \text{height} \times \text{length} \times \text{width}$. The liver, lungs, omentum and spleen were removed to allow checking of the typical routes of metastasis.

Inhibition of Proliferation In Vivo

Figure 2:
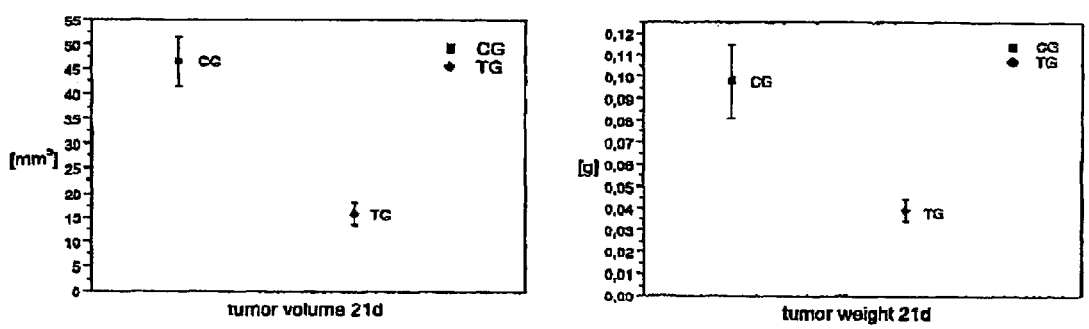
FIG. 2 is a graphical representation of dose dependence of the effect of treatment in accordance with an illustrative embodiment of the present invention.

The increase in volume and the increase in weight of the tumor for the 2 groups treated with the ODN 5'tocopheryl-TGC TCC CCC CTG GCT-3'-$PEG_{1500}$ (as phosphorothioate) (SEQ ID NO:1)are shown in FIGS. 1a and 1b respectively. The increase in weight and volume of the 2 groups is markedly less than that of the control groups. The volume of the tumors fell by 64% in the group that received intraperitoneal injection. Treatment using the subcutaneous continuous pump appears to be more effective still. The volume of the tumors had fallen by 70% after 21 days. Histological and histochemical investigation of the organs did not reveal any conspicuous findings. FIG. 2 shows the dose-dependence of the effect.

Figure 3:
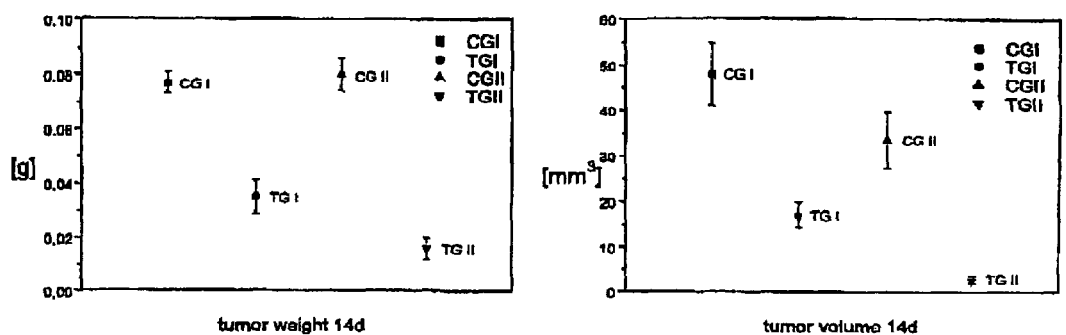
FIG. 3a is a graphical representation of changes in weight and volume of a selected group of tumors treated with another exemplary oligonucleotide in accordance with an illustrative embodiment of the present invention.
FIG. 3b is a graphical representation of changes in weight and volume of another selected group of tumors treated with another exemplary oligonucleotide in accordance with an illustrative embodiment of the present invention.
Figure 3:
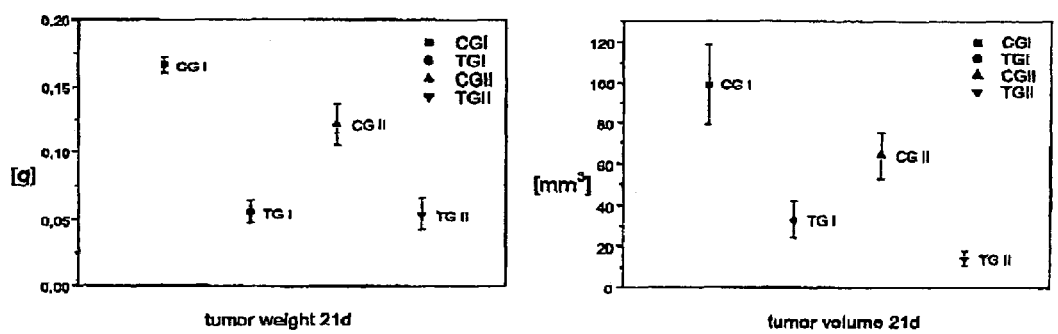

The volume of the tumor and weight of the tumor of the groups treated with ODN 5'-tocopheryl-CCT CGC TTC GCC CGT-3-$PEG_{1500}$ (SEQ ID NO:2) are shown in FIGS. 3a and 3b respectively. Treatment with ODN was commenced immediately after implantation of the human pancreas tumor. The volume and weight of the tumor similarly declined by approximately two-thirds.

This shows that the growth of human pancreatic tumors is not just stopped in vivo, but a marked reduction in the size of the tumor is achieved within 2-3 weeks. This is of exceptional importance since the pancreas adenocarcinoma cell line Panc-Tu-I used in vivo is a tumor cell line that is very resistant to apoptosis and is entirely resistant to numerous other treatment strategies, such as the triggering of programmed cell death by Fas/CD95 activation. TRAIL or chemotherapeutics.

The invention claimed is:

1. An oligonucleotide consisting of:
5'-tocopheryl-TGC TCC CCC CTG GCT-3'-PEG$_{1500}$ (SEQ ID NO:1); or
5'-tocopheryl-TGC TCC CCC CTG GCT-3'-tocopheryl (SEQ ID NO:1).

2. Pharmaceutical agent containing at least one oligonucleotide according to claim 1, and optionally pharmaceutically acceptable auxiliary agents.

* * * * *

UNITED STATES PATENT AND TRADEMARK OFFICE
CERTIFICATE OF CORRECTION

PATENT NO. : 7,608,705 B2  
APPLICATION NO. : 10/381869  
DATED : October 27, 2009  
INVENTOR(S) : Bayer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 822 days.

Signed and Sealed this

Twelfth Day of October, 2010

David J. Kappos  
*Director of the United States Patent and Trademark Office*

SEQUENCE LISTING

<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: synthetic construct

<400> SEQUENCE: 1 tgctccccc tggct                                                    15

<210> SEQ ID NO 2
<211> LENGTH: 15
<212> TYPE: DNA
<213> ORGANISM: Artificial Sequence
<220> FEATURE:
<223> OTHER INFORMATION: synthetic construct

<400> SEQUENCE: 2
cctcgcttcg cccgt                                                   15